US 6,656,195 B2

(12) United States Patent
Peters et al.

(10) Patent No.: US 6,656,195 B2
(45) Date of Patent: Dec. 2, 2003

(54) FLEXIBLE INNER TUBULAR MEMBERS AND ROTARY TISSUE CUTTING INSTRUMENTS HAVING FLEXIBLE INNER TUBULAR MEMBERS (75) Inventors: Gary Peters, Jacksonville, FL (US); Kenneth Adams, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 119 days.

(21) Appl. No.: 09/950,607

(22) Filed: Sep. 13, 2001

(65) Prior Publication Data
US 2002/0038129 A1 Mar. 28, 2002

Related U.S. Application Data
(60) Provisional application No. 60/234,333, filed on Sep. 22, 2000.

(51) Int. Cl.$^7$ ................................. A61B 17/22
(52) U.S. Cl. ...................................... 606/159
(58) Field of Search ................... 606/159, 170, 606/180, 171, 174, 169; 604/22

(56) References Cited

U.S. PATENT DOCUMENTS

| 177,490 | A | 5/1876 | Fones et al. |
|---|---|---|---|
| 4,203,444 | A | 5/1980 | Bonnell et al. |
| 4,445,509 | A | 5/1984 | Auth |
| 4,466,429 | A | 8/1984 | Loscher et al. |
| 4,646,738 | A | 3/1987 | Trott |
| 4,706,659 | A | 11/1987 | Matthews et al. |
| 5,152,744 | A | 10/1992 | Krause et al. |
| 5,322,505 | A | 6/1994 | Krause et al. |
| 5,411,514 | A | 5/1995 | Fucci et al. |
| 5,454,827 | A | 10/1995 | Aust et al. |
| 5,510,070 | A | 4/1996 | Krause et al. |
| 5,540,706 | A | 7/1996 | Aust et al. |
| 5,618,294 | A | 4/1997 | Aust et al. |
| 5,620,447 | A | 4/1997 | Smith et al. |
| 5,669,926 | A | 9/1997 | Aust et al. |
| 5,707,350 | A | 1/1998 | Krause et al. |
| 5,807,241 | A | 9/1998 | Heimberger |
| 5,851,208 | A | 12/1998 | Trott |
| 5,851,212 | A | 12/1998 | Zirpus et al. |
| 5,885,288 | A | 3/1999 | Aust et al. |
| 5,899,914 | A | 5/1999 | Zirps et al. |
| 5,922,003 | A | 7/1999 | Anctil et al. |
| 5,938,678 | A | 8/1999 | Zirps et al. |

Primary Examiner—Kevin T. Truong

(57) ABSTRACT

A flexible inner tubular member for being rotated in an outer tubular member of a rotary tissue cutting instrument includes an elongate inner tube having a rotatably driveable proximal end, a distal end having a cutting member exposed from the outer tubular member to cut anatomical tissue and a flexible region allowing the inner tubular member to rotate within the outer tubular member while conforming to the shape of the outer member. The flexible region is defined by a helical cut in the inner tube defining a plurality of integrally, unitarily connected tube segments angularly movable relative to one another and a spiral wrap disposed over the helical cut.

21 Claims, 4 Drawing Sheets

FLEXIBLE INNER TUBULAR MEMBERS AND ROTARY TISSUE CUTTING INSTRUMENTS HAVING FLEXIBLE INNER TUBULAR MEMBERS

CROSS-REFERENCE TO RELATED PATENT APPLICATIONS

This application claims priority from provisional patent application Ser. No. 60/234,333 filed Sep. 22, 2000 and entitled Flexible Inner Tubular Members and Rotary tissue Cutting Instruments Having Flexible Inner Tubular Members, the disclosure of which is incorporated herein by reference. This application is related to prior patent applications Ser. No. 09/495,359 filed Feb. 1, 2000 (now U.S. Pat. No. 6,312,438), Ser. No. 09/404,461 filed Sep. 24, 1999 (now U.S. Pat. No. 6,533,749) and Ser. No. 09/074,739 filed May 8, 1998 and now U.S. Pat. No. 5,922,003, the disclosures of which are incorporated herein by reference.

BACKGROUND OF THE INVENTION

1. Field of the Invention

The present invention relates generally to surgical cutting instruments having relatively movable inner and outer tubular members and, more particularly, to flexible inner tubular members for being rotatably received in the outer tubular members of surgical cutting instruments and to rotary tissue cutting instruments having flexible inner tubular members rotatably disposed within tubular outer members.

2. Discussion of the Related Art

Surgical cutting instruments in which an elongate inner member is rotated within an elongate, tubular outer member have become well accepted in surgical procedures where access to the surgical site is gained via a narrow portal or passage. Typically, the tubular outer member includes a distal end with an opening defining a cutting port or window and the inner member includes a distal end with a cutting tip for engaging bodily tissue via the opening. Proximal ends of the inner and outer members commonly include hubs which attach to a handpiece having a motor for rotating the inner member relative to the outer member. The distal end of the inner member can have various configurations dependent upon the surgical procedure to be performed, with the opening in the distal end of the outer member being suitably configured to cooperate with the particular configuration of the distal end of the inner member to cut, resect or abrade tissue. Often the inner member is tubular so that the loose tissue resulting from a cutting, resecting or abrading procedure can be aspirated through the lumen of the inner member. It is also common for the direction of rotation of the inner member to be reversible during operation. An example of a rotary tissue cutting instrument of the aforementioned type is described in U.S. Pat. No. 4,203,444 to Bonnell et al for use in performing arthroscopic knee surgery.

The tubular inner and outer members disclosed in the Bonnell et al patent are straight. In many surgical procedures, however, it is desirable for the cutting instruments to be bent or curved to access surgical sites which are generally not accessible with straight cutting instruments. For example, in arthroscopic knee surgery it is well known to use curved cutting instruments which can be positioned at various desired angles relative to the surface of the patella. While rotary tissue cutting instruments with curved or bendable shafts have been used for some time, as exemplified by U.S. Pat. No. 4,466,429 to Loscher et al and U.S. Pat. No. 4,445,509 to Auth, these shafts typically employ a single spirally wound strip of material to impart flexibility while transmitting torque. Unfortunately, spirally wound shafts and couplings tend to unwind when rotated in a direction opposite their winding so that torque can only be transmitted efficiently in one direction.

This problem is addressed in U.S. Pat. No. 177,490 to Fones et al wherein a flexible shaft for transmitting torque in both directions is disclosed having a plurality of coaxial spirally wound strips of material wound in alternating opposite directions relative to one another. U.S. Pat. No. 4,646,738 to Trott describes a rotary tissue cutting instrument for arthroscopic surgery which is similar to the instrument described in the Bonnell et al patent but with a flexible transmission element of the type disclosed in the Fones et al patent. The flexible transmission element of Trott is made up of three coaxial spirally wound strips of material interposed between separate proximal and distal end portions of the inner member to allow the inner member to bend. Proximal and distal end portions of the inner member include reduced diameter neck portions which are telescopically received within the innermost spiral strip to facilitate welding of the strips to the other components of the inner member. Disadvantages of this arrangement include the neck portions tending to stiffen the spiral strips in the vicinity of the cutting tip thereby preventing the inner member from bending adjacent the cutting tip and the inner member having an increased diameter. In addition, it is possible for the separate components to become detached from one another during use such that torque can no longer be effectively transmitted to the cutting tip.

U.S. Pat. No. 5,807,241 to Heimberger discloses a flexible tube, particularly useful as a shank for a flexible endoscope. The flexible tube is formed by cutting a gap in a closed path in a longitudinally straight rigid tube to form interlocking but completely materially or physically separated tube sections that allow the tube to bend axially. The flexible tube may not be well suited for use as a rotatable inner tubular member of a surgical cutting instrument since it may be limited by its torque capabilities to relatively low single direction and bi-direction rotational speeds. Also, it is possible for the individual tube sections to disengage or become detached when the tube is bent.

SUMMARY OF THE INVENTION

Accordingly, it is a primary object of the present invention to overcome the abovementioned disadvantages of the prior art and to improve the flexible inner tubular members of rotary tissue cutting instruments used in surgery of the head and neck and other parts of the body.

It is another object of the present invention to reduce the number of parts needed to form a rotatable flexible inner tubular member of a rotary tissue cutting instrument capable of operating at relatively high single direction speeds.

It is yet another object of the present invention to increase the torque capability of a rotatable flexible inner tubular member of a rotary tissue cutting instrument by forming the inner tubular member from a helically or spirally cut tube and at least one helical or spiral wrap applied over the cut region of the tube.

Still another object of the present invention is to facilitate bending of an angled rotary tissue cutting instrument adjacent the cutting tip thereof by forming the inner tubular member from a rigid tube that is cut to form interlocked, helical or spiral tube segments extending in series from a proximal portion of the tube to near the cutting tip and at least one spiral wrap disposed over the tube segments.

A further object of the present invention is to form a rotatable flexible inner tubular member of a rotary tissue cutting instrument from a rigid tube that is cut to form integrally, materially connected tube segments and a spiral wrap disposed over the tube segments.

The present invention is generally characterized in a flexible inner tubular member for being rotatably disposed in an outer tubular member to form a rotary tissue cutting instrument. The flexible inner tubular member is made from a rigid tube having a helical or spiral cut therein extending continuously in a helical or spiral path along the cylindrical wall of the tube and about a central longitudinal axis of the tube. The helical cut extends in the radial direction through the entire thickness of the cylindrical wall to form a plurality of integrally, unitarily connected helical or spiral tube segments creating a bendable region in the tube. The helical cut is formed in a dovetail pattern such that adjacent tube segments present tapered, straight-sided tenons interlocked with tapered, straight-sided mortises. At least a first spiral wrap is disposed over the helical cut and includes a first strip of material helically or spirally wound over the tube segments, with opposite ends of the strip of material being secured to the tube on opposite ends or sides of the helical cut. The helical cut defines an angle with the central longitudinal axis of the tube, and the strip of material is wound over the tube at an angle opposite the angle of the helical cut. A cutting member is disposed at a distal end of the tube. The helical cut and spiral wrap define a flexible region in the inner member to transmit torque as the inner member is rotated within and conforms to the shape of a bent or angled or a longitudinally straight outer tubular member. A second spiral wrap may be disposed over the first spiral wrap and includes a second strip of material spirally wound over the first strip of material, with opposite ends of the second strip of material being secured to the tube on opposite ends or sides of the helical cut. The second strip is wound over the tube at about the same angle and in the same direction as the angle of the helical cut.

Another aspect of the present invention is generally characterized in a rotary tissue cutting instrument including a rigid outer tubular member having open distal and proximal ends and a flexible inner tubular member rotatably disposed in the outer member. The inner member has a cutting member at its distal end, the cutting member being exposed from the distal end of the outer member to cut anatomical tissue as the inner member is rotated within the outer member. In one aspect of the rotary tissue cutting instrument, the outer member has proximal and distal length portions connected by a bend, and the inner member has a flexible region disposed within the bend to allow the inner member to flex or bend as it is rotated in the outer member. The inner member is formed by a rigid tube having a helical or spiral cut, which defines a bendable region, and a spiral wrap disposed over the helical cut. The helical cut extends continuously in a helical or spiral path along a cylindrical wall of the tube and about a central longitudinal axis of the tube. The helical cut extends radially through the entire thickness of the cylindrical wall to form a plurality of integrally, unitarily connected helical or spiral tube segments. The helical cut is formed in a dovetail pattern such that adjacent tube segments are interlocked. The spiral wrap is formed by a first strip of material wound over the tube segments and having its opposite ends secured to the tube. The helical cut and the spiral wrap form the flexible region in the inner member to transmit torque to the cutting member while the inner member conforms to the bend or angle of the outer member as the inner member is rotated in the outer member. In another aspect of the rotary tissue cutting instrument, a second strip of material is wound over the first strip of material and has its opposite ends secured to the tube so that an inner spiral wrap and an outer spiral wrap are disposed over the helical cut. The inner member may be provided with an aspiration port that is exposed from the distal end of the outer member, allowing tissue and fluids to be aspirated from an operative site through the inner member.

Some of the advantages of the present invention are that the number of parts needed to produce a rotary tissue cutting instrument are reduced; the rotary tissue cutting instrument can be bent close to the distal end of the instrument to improve access to an operative site; the size or diameter of the instrument can be minimized to facilitate access to an operative site and expand the areas of use for the instrument; the inner diameter of the inner member can be maximized to enhance aspiration therethrough and minimize clogging; the strength of the flexible inner member is increased; the inner member can be designed for single or bi-directional rotation; disengagement or detachment of adjacent tube segments when subjected to bending forces is deterred; and longitudinal and rotational displacements of the inner tube can be limited or controlled.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

DETAILED DESCRIPTION OF THE PREFERRED EMBODIMENTS

Figure 1:
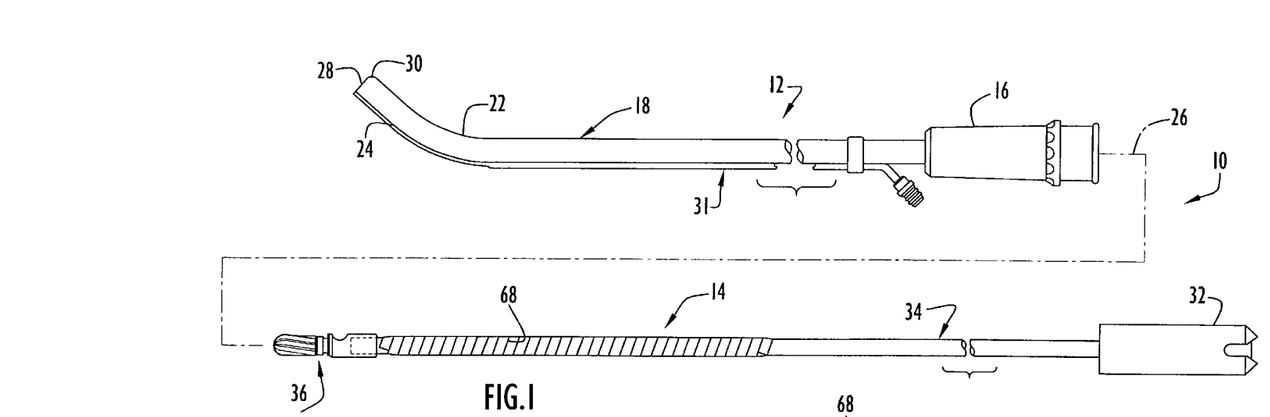
FIG. 1 is a broken, exploded side view of a rotary tissue cutting instrument according to the present invention.

A rotary tissue cutting instrument 10 according to the present invention, as illustrated in FIG. 1, includes an outer tubular member 12 and a flexible inner tubular member or blade 14 rotatably received within the outer member. Outer member 12 includes an outer hub 16 and a rigid outer tube or shaft 18 having a proximal length portion 20 of longitudinally or axially straight configuration extending distally from the hub to a bend, angle or curve 22 connecting the proximal length portion with a distal length portion 24 of longitudinally or axially straight configuration oriented at an angle relative to a central longitudinal axis 26 of the proximal length portion. Distal length portion 24 extends upwardly from bend 22, looking at FIG. 1, to an open distal end 28 defining an opening circumscribed by a peripheral or circumferential edge. A curved recess, notch or indentation 30 may be formed in outer tube 18 along the circumferential edge, the recess 30 extending in a proximal direction and being disposed at the top of the outer tube when the outer member is oriented as shown in FIG. 1. The outer member may be the same or similar to the outer member disclosed in prior application Ser. No. 09/495,350 filed Feb. 1, 2000, the disclosure of which is incorporated herein by reference. Accordingly, the outer member may include an irrigation passage 31 as disclosed in the aforementioned application. The radius of curvature for the bend, the size of the bend angle, the location of the bend relative to the distal end of the outer member, and the direction of the bend are dependent upon the procedure to be performed and the location of an operative site or area to be accessed. For example, the outer member can have any of the configurations described in U.S. patent applications Ser. No. 09/404,461 filed on Sep. 24, 1999 and Ser. No. 09/074,739 filed on May 8, 1998 and now U.S. Pat. No. 5,922,003, the disclosures of which are incorporated herein by reference.

Figure 2:
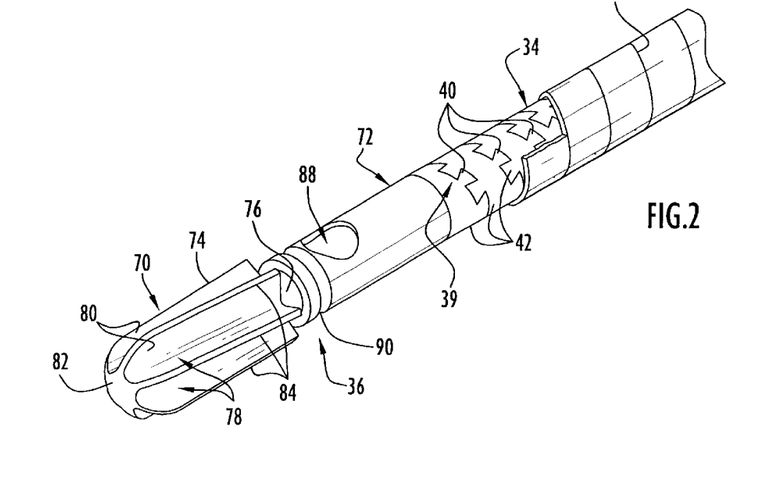
FIG. 2 is an enlarged fragmentary perspective view, partly cut away, of the distal end of a flexible inner tubular member according to the present invention used in the rotary tissue cutting instrument.
Figure 3:
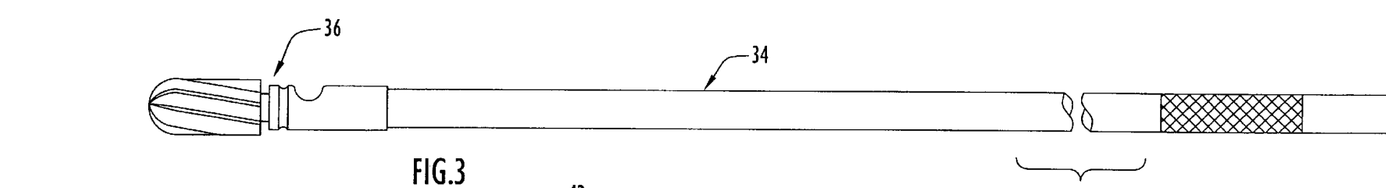
FIG. 3 is a broken side view of a rigid tube used in formation of the flexible inner tubular member.
Figure 4:
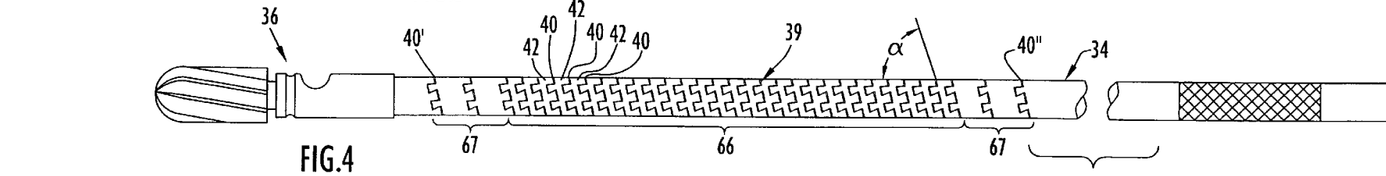
FIG. 4 is a broken side view of the tube with a helical cut formed therein creating a plurality of integrally, unitarily connected helical tube segments.

As shown in FIG. 1, inner member 14 includes an inner hub 32 disposed proximally of the outer hub when the inner member is disposed within the outer member, an elongate inner tube or shaft 34 extending distally from the inner hub to be disposed coaxially or concentrically within the outer tube, and a cutting member 36 disposed at a distal end of the inner tube. Inner tube 34 is formed from a rigid tube made of medically acceptable material such as stainless steel. Tube 34 has a hollow cylindrical configuration with a cylindrical wall defining a lumen entirely through tube 34. As best seen in FIGS. 2 and 4, a helical or spiral cut 39 is formed through the cylindrical wall of tube 34, which is illustrated in FIG. 3 prior to formation of the helical cut 39. The helical cut 39 has a plurality of angled cut segments 40 on opposing sides of the tube 34, the angled cut segments 40 for the left side of tube 34, looking distally, being shown in FIGS. 2 and 4. The angled cut segments 40 are axially or longitudinally spaced from one another lengthwise along the tube 34 to form a plurality of serially arranged, interconnected helical or spiral tube segments 42 between the cutting member 36 and a proximal end of the inner tube 34.

The helical cut 39 is preferably formed in rigid tube 34 by laser cutting. The helical cut 39 extends continuously in a helical or spiral path, i.e. an open path, along the cylindrical wall forming tube 34 and about a central longitudinal axis of tube 34, such that opposite ends of the helical cut do not meet. The helical cut 39 extends in the radial direction through the entire thickness of the cylindrical wall so that each angled cut segment 40 is disposed between a pair of adjacent tube segments 42. Since the helical cut 39 extends continuously in the helical or spiral path, the tube segments 42 are materially or physically connected or joined to one another, with adjacent tube segments being integrally, unitarily connected in a helical or spiral fashion. The helix angle α for helical cut 39 results in the angled cut segments 40 being disposed at angle a relative to the central longitudinal axis of tube 34 as shown in FIG. 4. The helical cut 39 extends around the central longitudinal axis of the inner tube in a first direction, the helical cut 39 extending about the central longitudinal axis of inner tube 34 with a clockwise or right hand turn or slant looking from distal to proximal, such that the angled cut segments 40 on the left side of tube 34 extend proximally with a downward slant at angle a relative to the central longitudinal axis of tube 34 as shown in FIG. 4. Of course, it should be appreciated that the angled cut segments on the right side of tube 34 extend distally with a downward slant at angle a relative to the central longitudinal axis of tube 34.

Figure 5:
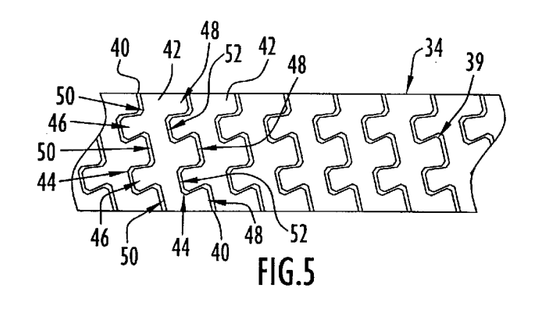
FIG. 5 is an enlarged fragmentary view of the cut region of the tube.

The helical cut 39 is formed in a dovetail pattern resulting in interlocked tenons and mortises at the junction of adjacent tube segments 42, which are separated by a small gap 44 corresponding to the width of helical cut 39 as shown in FIG. 5. Still referring to FIG. 5, each tube segment 42 has one or more distal tenons 46, one or more proximal tenons 48, one or more distal mortises 50, and one or more proximal mortises 52. In the flexible inner tubular member 14, each tube segment 42 has a plurality of distal tenons 46, a plurality of proximal tenons 48, a plurality of distal mortises 50 disposed between the distal tenons, respectively, and a plurality of proximal mortises 52 disposed between the proximal tenons, respectively. The distal tenons 46 are disposed in the proximal mortises, respectively, of the next distal or distally adjacent tube segment, and the proximal tenons 48 are disposed in the distal mortises, respectively, of the next proximal or proximally adjacent tube segment. Similarly, the distal mortises 50 receive or accommodate the proximal tenons, respectively, of the next distal tube segment, and the proximal mortises 52 receive or accommodate the distal tenons, respectively, of the next proximal tube segment. The tenons and mortises for tube 34 have matching or complementary configurations; however, the tenons can have a configuration different from the configuration of the mortises while still limiting separation of the tube segments.

Figure 6:
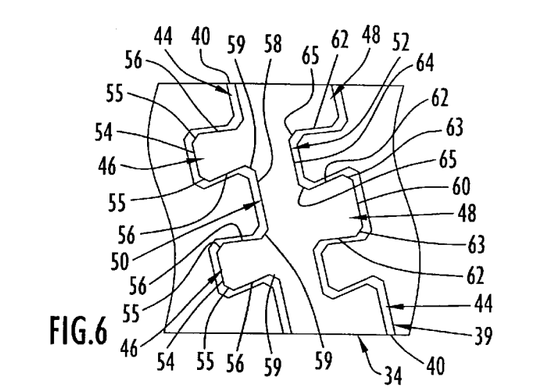
FIG. 6 is a further enlarged fragmentary view of the cut region of the tube.

As shown in FIG. 6, each distal tenon 46 has a straight-sided, tapered configuration with a straight forward edge 54 and straight side edges 56 extending angularly inwardly toward one another from chamfered or angled outside corners 55 joining the forward edge 54 to the side edges 56, respectively. The side edges 56 of angularly adjacent distal tenons, i.e. distal tenons that are adjacent one another with respect to their angular spacing about the central longitudinal axis of the tube 34, form the side edges of the distal mortise disposed between the angularly adjacent distal tenons. Thus, each distal mortise 50 has a straight-sided, tapered configuration with a straight base edge 58 and straight side edges 56 joined to base edge 58 by chamfered or angled inside corners 59, respectively. The side edges 56 extend angularly inwardly toward one another from inside corners 59 to the outside corners 55 of the angularly adjacent distal tenons between which the distal mortise is disposed. The forward edges 54 for an individual angled cut segment 40 are disposed in a plane oriented at angle α to the central longitudinal axis of tube 34 as shown in FIG. 4, and the base edges 58 thereof are disposed in a plane parallel to but spaced proximally from the plane of the forward edges 54.

Referring still to FIG. 6, each proximal tenon 48 has a straight-sided, tapered configuration with a straight proximal edge 60 and straight side edges 62 extending angularly inwardly toward one another from chamfered or angled outside corners 63 joining the proximal edge 60 to the side edges 62, respectively. The side edges 62 of angularly adjacent proximal tenons form the side edges of the proximal mortise disposed between the angularly adjacent proximal tenons. Thus, each proximal mortise 52 has a straight-sided, tapered configuration with a straight base edge 64 and straight side edges 62 joined to base edge 64 by chamfered or angled inside corners 65, respectively. The side edges 62 extend angularly inwardly toward one another from inside corners 65 to the outside corners 63 of the angularly adjacent proximal tenons between which the proximal mortise is disposed. The proximal edges 60 for an individual angled cut segment 40 are parallel to forward edges 54 and, therefore, are disposed in a plane oriented at angle α to the central longitudinal axis of tube 34, and the base edges 64 thereof are disposed in a plane parallel to but spaced distally from the plane of the proximal edges 60. In the case of tube 34, the forward edges 54 are joined to side edges 56 at chamfered or angled outside corners, the base edges 58 are joined to side edges 56 at chamfered or angled inside corners, the proximal edges 60 are joined to side edges 62 at chamfered or angled outside corners, and the base edges 64 are joined to side edges 62 at chamfered or angled inside corners. However, any or all of the outside or inside corners can be radiused or sharp as described further below.

As shown in FIG. 4, the helical cut 39 defines a distal most angled cut segment 40' close to the cutting member 36, a proximal most angled cut segment 40" and one or more intermediate angled cut segments disposed therebetween, with a helically or spirally cut region being defined between the distal most and proximal most angled cut segments. The cut region extends less than the entire length of the inner tube 34 with there being uncut regions distally and proximally, respectively, of the cut region. Adjacent tube segments 42 can move angularly relative to one another, such that the helically cut region defines a bendable region allowing the tube 34 to bend or flex between the distal most and proximal most angled cut segments. The longitudinal spacing between the plane containing the forward edges 54 and the plane containing the base edges 64 of a tube segment 42 defines a pitch for helical cut 39 and for the angled cut segments 40. The helical cut 39 and angled cut segments 40 have a uniform first pitch along a central portion 66 of the cut region and a uniform second pitch, greater than the first pitch, along distal and proximal end portions 67 of the helically cut region. In this manner, increased flexibility is provided in the central portion 66 while increased torsional strength is provided in the distal and proximal end portions 67, which define transitional areas between the central portion and uncut regions of the tube 34. The uncut region of tube 34 distally of the distal most angled cut segment 40' is of sufficient length to permit the inner tube 34 to be coupled with the cutting member as explained below while allowing the inner tube to bend or flex close to or just proximally of the cutting member thereby facilitating use of the cutting instrument in hard to reach areas sometimes encountered in surgery of the head and neck and other parts of the body.

Figure 7:
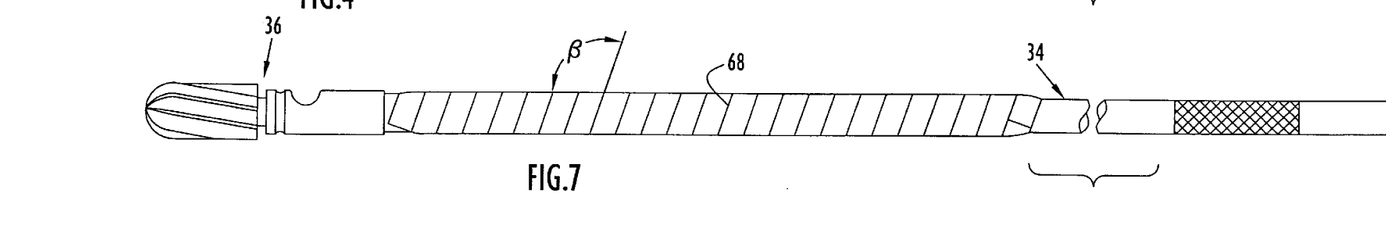
FIG. 7 is a broken side view of the tube with a spiral wrap disposed over the tube segments to form the flexible inner tubular member.

Inner member 14 further includes at least one spiral wrap formed by a helically or spirally wound strip 68 superimposed over the helically cut region of tube 34 as shown in FIGS. 1, 2 and 7. Strip 68 is formed of a resilient or elastic material, such as stainless steel, and preferably has a rectangular cross-section allowing the strip to lay flat when wrapped or wound around the cut region of the tube 34. Strip 68 is wrapped around tube 34 in a direction opposite to the turn or slant of helical cut 39 and angled cut segments 40. The strip 68 is thusly wound around tube 34 in a second direction, opposite the first direction of helical cut 39. The strip 68, therefore, has a counter clockwise or left hand turn or slant looking from distal to proximal in FIG. 7. The strip 68 may be oriented at an angle β which is the supplement of angle α (i.e., 180° minus α). The strip 68 is superimposed over all of the angled cut segments 40, and opposite ends of the strip 68 are secured to the inner tube 34, for example, by laser welding the ends 360° about the circumference of the tube 34 on opposite ends or sides of helical cut 39. The helically cut region of tube 34 and the spiral wrap formed by strip 68 define a flexible region in the inner member 14 to transmit torque from a motorized handpiece (not shown) to the cutting member while allowing the inner member 14 to conform to the bent or angled shape of the outer member 12 as the inner member 14 is rotated within the outer member.

Figure 8:
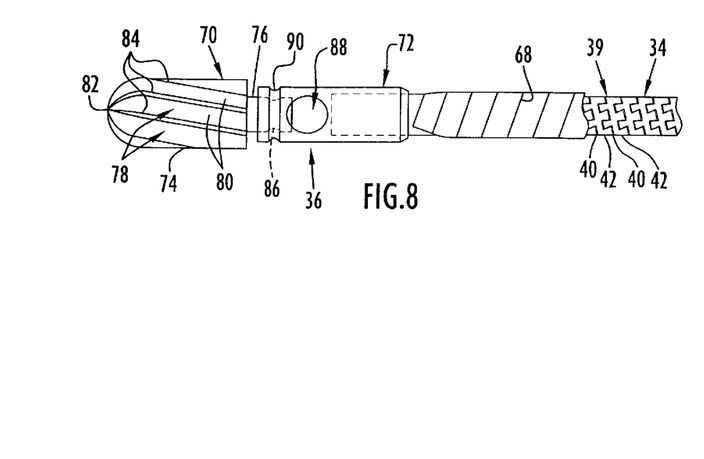
FIG. 8 is a broken top view of the distal end of the flexible inner tubular member according to the present invention.
Figure 9:
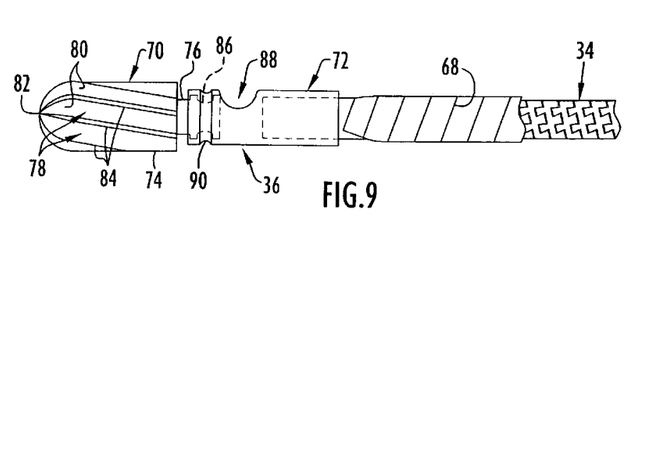
FIG. 9 is a broken side view of the distal end of the flexible inner tubular member according to the present invention.

As best seen in FIGS. 2, 8 and 9, the cutting member 36 includes a bur tip 70 and an adapter or coupling 72 by which the bur tip is coupled to the distal end of inner tube 34. The bur tip 70 includes a bullet-shaped bur body 74 and a neck 76 extending proximally from the bur body to be disposed within the adapter as explained further below. A plurality of flutes 78 are formed in the bur body to define cutting surfaces 80 emanating from a distal end 82 of the bur tip 70, the distal end 82 defining a distal end for the cutting member 36 as well as the inner member 14. The flutes 78 and, therefore, the cutting surfaces 80 extend longitudinally at an angle to a longitudinal axis of the bur tip. The flutes are formed so that the cutting surfaces 80 are curved or angled toward the clockwise direction looking proximally in FIG. 1 and terminate at cutting edges 84. The neck 76 is of cylindrical configuration and is diametrically smaller than the bur body. The neck terminates at a proximal end defining a proximal end of the bur tip, and an annular groove 86 is formed in neck 76 between the proximal end thereof and bur body 74 as shown in FIGS. 8 and 9.

The adapter 72 comprises a hollow cylindrical or tubular member having a passage or lumen extending longitudinally therethrough and having open distal and proximal ends communicating with the lumen. The open distal end of the adapter is designed to receive the neck 76 of the bur tip while the open proximal end of the adapter is designed to receive the distal end of inner tube 34. An opening or port 88 is formed in the adapter in communication with the lumen thereof and faces laterally outwardly of the inner member. The port 88 defines an aspiration or suction port for the inner member. The bur tip 70 and the adapter 72 can be of the type disclosed in prior application Ser. No. 09/495,350, the disclosure of which was incorporated herein by reference. Although the adapter 72 is shown as a separate component or part, it should be appreciated that the adapter can be incorporated into a single-piece cutting member including bur tip 70 and adapter 72, thereby reducing cost and the number of components.

The inner member 14 is assembled by securing the neck of the bur tip to the distal end of the adapter and securing the distal end of the inner tube to the proximal end of the adapter. When so assembled, the lumen of the adapter and the lumen of the inner tube are continuous with one another and define an aspiration or suction passage within the inner member. One manner of assembling the inner member involves inserting the distal end of the inner tube into the proximal end of the adapter and laser welding the inner tube to the adapter. The neck of the bur tip is inserted in the distal end of the adapter so that the groove is disposed in the adapter lumen with the bur body disposed distally of the adapter distal end. Thereafter, the adapter is crimped and laser welded to the neck. Preferably, the adapter is crimped at a location aligned with the groove of the neck so that a crimped portion 90 of the adapter enters and is disposed in the groove as shown in FIGS. 8 and 9. The port 88 is located substantially between the neck of the bur tip and the distal end of the inner tube so as to be substantially unobstructed thereby. Hub 32 is attached to inner tube 34 in a conventional manner using a raised fine diamond knurl at the proximal end of the inner tube as a point of attachment.

The outer hub 16 and inner hub 32 are designed for releasable or removable coupling with a powered surgical handpiece capable of rotating the inner member within the outer member while the outer member is rigidly secured to the handpiece. In a preferred embodiment, the hubs are designed for use with the STRAIGHTSHOT® handpiece of Medtronic Xomed Surgical Products, Inc. of Jacksonville, Fla. and disclosed in U.S. Pat. No. 5,916,231 to Bays, the disclosure of which is incorporated herein by reference.

The rotary tissue cutting instrument 10 is assembled for use by inserting cutting member 36 of inner member 14 into the proximal end of outer hub 16 and advancing the inner member distally so that the bur tip 70 is exposed from the distal end of the outer tube. When the inner member is fully inserted and advanced within the outer member, the aspiration port 88 will be disposed proximally of the cutting edges or surfaces and will be disposed close to, adjacent or in alignment with the open distal end of the outer member. The aspiration port can be substantially aligned with the peripheral edge of the outer tube to be exposed by the outer member a maximum amount when aligned with the center of notch 30 and to be exposed less than the maximum amount when not aligned with the notch as the inner member rotates within the outer member.

In use, hubs 16 and 32 are connected to a conventional motorized surgical handpiece (not shown), such as the STRAIGHTSHOT® marketed by Medtronic Xomed Surgical Products, Inc., such that the outer member 12 is held substantially stationary relative to the handpiece while permitting inner member 14 to rotate within the outer member. At this point, the inner member is disposed concentrically within the outer member, the adapter 72 acting as a bearing member or bearing surface within the outer tube to keep the inner member concentric while rotating. The flexible region of the inner member is disposed within the bend of the outer member. When the handpiece motor is actuated, the outer member remains substantially stationary relative to the handpiece while the inner member and its hub are rotated, the flexible region allowing the inner member to bend as it is rotated. The use of strip 68 forming a spiral wrap over tube segments 42 allows the inner member to be safely rotated at relatively higher single direction speeds, i.e. 12,000 rpm or greater, to transmit higher torque and to effect increased aspiration. Irrigating fluid can be supplied to the operative site via the irrigation passage 31. Suction applied through the inner member via the handpiece is applied at the operative site or area via the aspiration port 88. The bur tip 70 produces both side and end cutting, and the aspiration port 88 serves to aspirate or evacuate blood, saline and the majority of resected tissue since most of the tissue resection occurs along the flutes. Since the aspiration port is in communication with the lumen of the inner tube, tissue and fluids are aspirated entirely through the inner member and handpiece.

Figure 10:
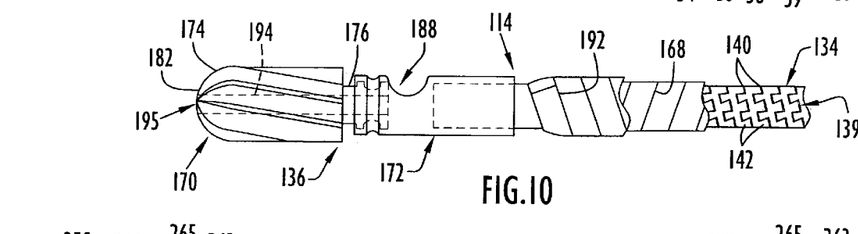
FIG. 10 is a broken side view of the distal end of a modified flexible inner tubular member according to the present invention.

An alternative flexible inner tubular member according to the present invention is illustrated in FIG. 10 at 114. Inner member 114 is similar to inner member 114 except that an aspiration passage is provided entirely through the cutting member 136 of inner member 114 and an additional spiral wrap is provided over the spiral wrap formed by strip 168, which is similar to strip 68. The cutting member 136 is similar to cutting member 36 except that a passage 194 extends longitudinally, coaxially, entirely through the bur tip 170 and has an opening or port 195 at the distal end 182 of the bur tip. The opening 195 faces distally, forwardly or to the front of the bur tip and defines a distal aspiration or suction port for the inner member 114 while the port 188, which is similar to port 88, defines a proximal aspiration or suction port for the inner member 114. The passage 194 extends through the bur body 174 and the neck 176 of bur tip 170 so as to communicate with the lumen of adapter 172. The passage through the bur tip and the lumen of the adapter 172 are continuous with one another to define an aspiration passage entirely through the cutting member 136. The aspiration passage entirely through the cutting member 136 and the lumen of the inner tube 134 are continuous with one another and define a continuous aspiration or suction passage entirely through the inner member 114. Although the inner member 114 is disclosed with two aspiration ports 188 and 195, it should be appreciated that additional aspiration at the distal aspiration port 195 can be effected by eliminating the proximal aspiration port 188. Adapter 172 is illustrated as a separate component or part, but may alternatively be formed integrally, unitarily with the bur tip 170.

Inner tube 134 is similar to inner tube 34 and includes helical cut 139 defining angled cut segments 140 and interlocked and materially or physically connected tube segments 142. A spiral wrap formed by strip 168 is superimposed over the tube segments 142 and is similar to the spiral wrap formed by strip 68. Inner tubular member 114 also includes an additional spiral wrap superimposed over the spiral wrap formed by strip 168. The additional spiral wrap is formed by strip 192, which is an outer spiral wrap, disposed over the spiral wrap formed by strip 168, which is an inner spiral wrap. The outer spiral wrap formed by strip 192 is similar to the inner spiral wrap formed by strip 168 but is wrapped or wound around the inner tube 134 in a direction opposite that of the inner spiral wrap. Therefore, the strip 192 is wrapped with a right hand or clockwise turn or slant looking from distal to proximal. Strip 192, which may be considered an outermost strip, and strip 168, which may be considered an innermost strip, are angled relative to one another (e.g., at supplementary angles relative to the central longitudinal axis of inner tube 134) so as to overlap one another. Since the innermost strip 168 is oriented at an angle β which is the supplement of angle α (i.e., 180° minus α) as described for inner member 14, the outermost strip 192 is oriented at the same angle α as the helical cut 139 and angled cut segments 140 thereof. Opposite ends of the outermost strip 192 are secured to the inner tube, for example by laser welding the ends 360° about the circumference of the inner tube at opposite ends or sides of helical cut 139.

Assembly and use of the inner member 114 in a rotary tissue cutting instrument is similar to that described above for inner member 14, with the flexible region defined by helical cut 139 and the innermost and outermost strips 168 and 192 allowing the inner member 114 to bend while being rotated within a bent or angled outer member. Suction applied through the inner member 114 via the handpiece is applied at the operative site or area via the distal aspiration port 195 at the distal end of the bur tip and the proximal aspiration port 188 disposed proximally of the bur body, since the passage through the bur tip, the lumen of the adapter and the lumen of the inner tube form a continuous suction or aspiration passage through the inner member. The proximal aspiration port 188 serves to aspirate or evacuate blood, saline and the majority of the resected tissue since most of the tissue resection occurs along the flutes. The distal aspiration port 195 serves to evacuate tissue, blood and saline, but primarily blood and saline since less tissue is resected at the distal end of the bur tip. The distal aspiration port thusly prevents accumulation of fluids and tissue debris at the distal end of the bur tip and thereby enhances endoscopic visualization of the bur tip during the procedure being performed. Suction provided by the distal aspiration port is maintained while the inner member is rotated, providing enhanced visibility of the bur tip by an endoscope throughout the procedure. Clogging, although unexpected, can be cleared by removing the instrument from the operative site and pushing a stylet through the passage of the bur tip to reach the obstruction, which is easier, faster and less complicated to perform than the declogging procedures required for conventional rotary tissue cutting instruments.

Figure 11:
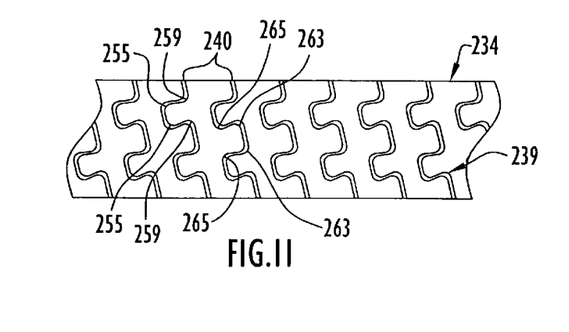
FIG. 11 is an enlarged fragmentary view of an alternative tube for a flexible inner tubular member according to the present invention having a modified helical cut.

A modified inner tube for the flexible inner members according to the present invention is illustrated at 234 in FIG. 11. Inner tube 234 has helical cut 239 and is similar to inner tube 34, except that the outside corners 255 of the distal tenons, the inside corners 259 of the distal mortises, the outside corners 263 of the proximal tenons, and the inside corners 265 of the proximal mortises are all rounded or radiused.

Figure 12:
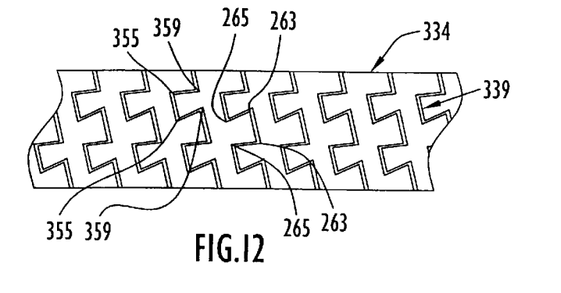
FIG. 12 is an enlarged fragmentary view of another alternative tube for a flexible inner tubular member according to the present invention having a further modified helical cut.

FIG. 12 illustrates at 334 another modification of an inner tube for the flexible inner members according to the present invention. Inner tube 334 has helical cut 339 and is similar to inner tube 34, except that the outside corners 355 of the distal tenons, the inside corners 359 of the distal mortises, the outside corners 363 of the proximal tenons, and the inside corners 365 of the proximal mortises are all sharp corners.

Figure 13:
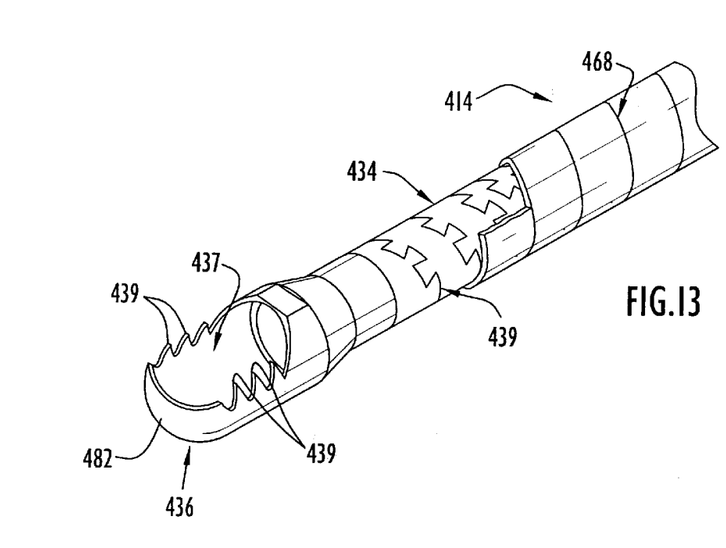
FIG. 13 is an enlarged fragmentary perspective view, partly cut away, of the distal end of another modified flexible inner tubular member according to the present invention.

Another alternative flexible inner tubular member according to the present invention is illustrated in FIG. 13 at 414. Inner member 414 is similar to inner member 14 except that the cutting member 436 for inner member 414 is integral and unitary with inner tube 434 and has a cutting configuration different from the cutting configuration of cutting member 36. The inner member 414 includes inner tube 434 having helical cut 439 and a spiral wrap 468 disposed over helical cut 439. An expanded, closed distal end of inner tube 434 defines cutting member 436 of greater diametric or cross-sectional size than the body of tube 434. The cutting member 436 terminates at a rounded distal end 482 and is cut to define a cutting port, opening or window 437. The cutting port 437 defines an aspiration port in communication with the lumen of inner tube 434. Edges of cutting member 436 on opposite sides of cutting port 437 are formed with a plurality of longitudinally extending cutting teeth 439, respectively. The aspiration port defined by cutting port 437 and the lumen of the inner tube 434 defines a continuous aspiration or suction passage entirely through inner member 414. Outer member 412 is illustrated as having an irrigation passage 431, similar to irrigation passage 31 of outer member 12, extending externally along the outer member. Accordingly, instruments 10 and 410 are representative of instruments in which irrigation for the blades is provided externally. However, it should be appreciated that irrigation for the blades may be provided externally or internally as disclosed in the patents incorporated herein by reference.

Figure 14:
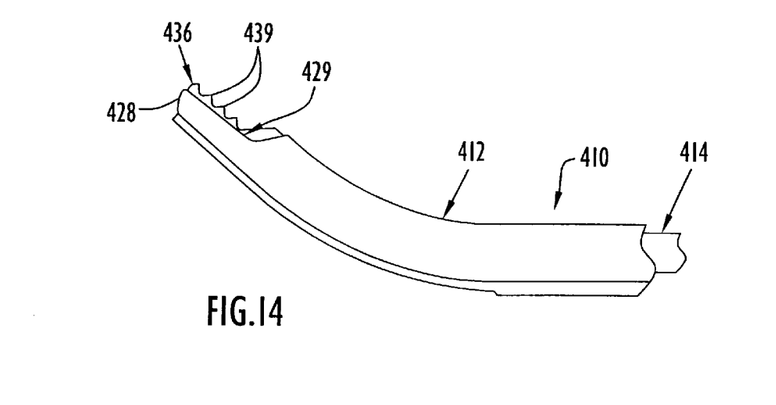
FIG. 14 is a broken side view of the distal end of a modified rotary tissue cutting instrument according to the present invention including the flexible inner tubular member of FIG. 13.

FIG. 14 illustrates a distal portion of an alternative rotary tissue cutting instrument 410 including inner member 414. The rotary tissue cutting instrument 410 is similar to the rotary tissue cutting instrument 10 and includes bent or angled outer tubular member 412 rotatably receiving inner member 414. The outer tubular member 412 is similar to the outer tubular member 12 except that its distal end 428 is formed with a cutting port, opening or window 429 from which the cutting member 436 is exposed when the inner member 414 is assembled with the outer member 412. As the inner member 414 is rotated relative to the outer member 412, anatomical tissue adjacent to the distal end of the instrument is cut by teeth 439 moving past the cutting opening 429 of the outer tubular member. The edges of cutting opening 429 can be sharp to cooperate with the cutting teeth 439 of the inner member. Of course, it should be appreciated that the edges of the cutting opening 429 can be straight as shown for outer member 412, curved or may be provided with cutting teeth cooperative with the cutting teeth 439.

In a preferred embodiment for an inner member according to the present invention, the inner tube is formed of type 304L stainless steel tubing, ¾ hard, with an inner diameter of about 0.102 inch and an outer diameter of about 0.122 inch. The helical cut can be formed using any suitable technique but is preferably formed by laser cutting. The inner tube has an overall length prior to attachment to the inner hub of about 6.49 inches. The distal most angled cut segment of the helical cut is disposed about 0.70 inch proximally of the distal end of the cutting member, and the proximal most angled cut segment of the helical cut is disposed about 2.40 inches proximally of the distal end of the cutting member. The distal angled cut segment of the central portion 66 is disposed about 0.90 inch from the distal end of the cutting member. The proximal angled cut segment of the central portion is disposed about 2.2 inches from the distal end of the cutting member. The helical cut is preferably oriented at an angle $\alpha$ of about 70° relative to the central longitudinal axis of the inner tube. The corners of the tenons and mortises have a 0.005 inch chamfer. The first or innermost strip is formed of type 302 stainless steel flat strip, full hard, with a width of about 0.05 inch and a thickness of about 0.006 inch. The innermost strip is wrapped at an angle $\beta$ of about 110° relative to the central longitudinal axis of the inner tube. The second or outermost strip, where provided, is preferably formed of the same material as the first or innermost strip and with the same configuration; however, the outermost strip is preferably oriented at the same angle $\alpha$ as the helical cut. The outermost strip begins and ends about the same distances from the distal end of the cutting member as the innermost strip, which begins about 0.68 inch proximally of the distal end of the cutting member and ends about 2.42 inches proximally of the distal end of the cutting member.

Use of a helical cut and one or more spiral wraps to impart flexibility to the inner member allows the external diametric or cross-sectional size of the inner tube to be minimized. Accordingly, the external diametric or cross-sectional side of the outer member can also be minimized. Minimization of the outer member external diameter as achieved with the present invention further improves the surgeon's visibility and increases the amount of free area available to the surgeon in which to maneuver the instruments and the endoscopes. By using a helical cut in the inner tube with at least one overlying spiral wrap, the diametric or cross-sectional size of the inner tube lumen is not reduced and, therefore, can be maximized to enhance aspiration of tissue and fluids through the inner member.

The rotary tissue cutting instruments of the present invention can be provided with or without bends, angles or curves. Accordingly, the flexible inner members can be used with outer members that are axially or longitudinally straight between their distal and proximal ends. Where bends are provided in the outer members, the locations of the bends as well as the sizes of the bend angles can be varied depending on the procedure to be performed. The rotary tissue cutting instruments according to the present invention can be bent anywhere along the length of the outer members so long as the inner members are provided with a flexible region located in juxtaposed relation to the bends. If desired, more complex curvatures and configurations can be formed by bending the outer tubes in more than one location and providing the inner members with one or more flexible regions in juxtaposed relation to the bends. The distal ends of the outer members can have various configurations in accordance with the configurations of the cutting members. The outer members can be of any desired length to obtain a desired constant or variable exposure of the cutting members and/or the aspiration port.

The flexible inner members according to the present invention can incorporate various cutting members of diverse configurations including the cutting members disclosed in the prior applications incorporated herein by reference. The helical cut can be formed in the inner tube in various ways. The number of mortises and tenons defined by the helical cut can vary, and the helical cut can be of uniform or variable pitch. The helical cut can be disposed at various angles and can be formed with either a left hand or right hand turn or slant. The specific geometry for the tenons and mortises may vary and is not limited to a dovetail design. The angles for the innermost and outermost strips can be optimally selected in accordance with the angle of the helical cut, and the innermost and outermost strips can be wound in either the clockwise or counterclockwise directions.

The dimensions listed above are merely exemplary and can be varied dependent upon the operational requirements of the instruments and the procedures. The features of the embodiments described above can be combined in any manner desired dependent upon the operational requirements of the procedure to be performed and the complexity of the rotary tissue cutting instruments. Depending upon the cutting members employed, the instruments of the present invention can be used to cut soft and bony tissue in humans and animals.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A flexible inner tubular member for being rotated in an outer tubular member of a rotary tissue cutting instrument to cut anatomical tissue, said flexible inner tubular member comprising
   an elongate inner tube of integral one-piece construction having a central longitudinal axis, a rotatably driveable proximal end, a distal end at which a cutting member is disposed to cut anatomical tissue, a cylindrical wall defining a lumen in said inner tube, and a helical cut formed in said inner tube extending lengthwise along said cylindrical wall in a helical path about said central longitudinal axis and extending radially through said cylindrical wall, said helical cut extending around said central longitudinal axis in a first direction, said helical cut defining a plurality of serially arranged helical tube segments with adjacent ones of said tube segments being integrally, unitarily connected to each other, said helical cut being formed in a dovetail pattern with adjacent ones of said segments interlocked by at least one tenon in interlocking engagement with at least one mortise, said helical cut defining a helix angle of about 70° with said central longitudinal axis; and
   a spiral wrap disposed over said helical cut including a strip of material wound over said inner tube in a second direction, opposite said first direction, and having ends secured to said inner tube, said spiral wrap being oriented on said inner tube at an angle of about 110° supplementary to said helix angle, said helical cut and said spiral wrap defining a flexible region in said inner tubular member allowing said inner tubular member to be rotated within the outer tubular member while conforming to the shape of the outer tubular member.

2. A flexible inner tubular member as recited in claim 1 wherein said spiral wrap is a first spiral wrap, said strip of material is a first strip of material, and further including a second spiral wrap disposed over said first spiral wrap and including a second strip of material wound over said first strip of material in said first direction and having ends secured to said inner tube, said second spiral wrap being oriented on said inner tube at an angle substantially the same as said helix angle.

3. A flexible inner tubular member as recited in claim 1 wherein said at least one tenon and said at least one mortise have straight inside and outside corners.

4. A flexible inner tubular member as recited in claim 1 wherein said at least one tenon and said at least one mortise have chamfered inside and outside corners.

5. A flexible inner tubular member as recited in claim 1 wherein said at least one tenon and said at least one mortise have radiused inside and outside corners.

6. A flexible inner tubular member as recited in claim 1 wherein said helical cut is formed by laser cutting said inner tube.

7. A flexible inner tubular member for being rotated in a longitudinally bent outer tubular member of a rotary tissue cutting instrument to cut anatomical tissue, said flexible inner tubular member comprising
   an elongate inner tube of integral one-piece construction having a central longitudinal axis, a rotatably driveable proximal end, a distal end at which a cutting member is disposed to cut anatomical tissue, a cylindrical wall defining a lumen in said inner tube, and a helical cut formed in said inner tube extending lengthwise along said cylindrical wall in a continuous helical path about said central longitudinal axis and extending radially through said cylindrical wall to define a plurality of integrally, unitarily connected helical tube segments, said helical cut forming interlocked tenons and mortises in adjacent ones of said tube segments, said adjacent ones of said tube segments being movable angularly relative to one another, said helical cut defining a helically cut region in said inner tube having a distal end portion, a proximal end portion and a central portion between said distal and proximal end portions, said helical cut having a uniform first pitch along said central portion and a uniform second pitch, greater than said first pitch, along said distal and proximal end portions; and a spiral wrap disposed over said tube segments including a strip of material wound over said inner tube at an angle opposite said helical cut and having ends secured to said inner tube, said helical cut and said spiral wrap defining a flexible region in said inner tubular member allowing said inner tubular member to be rotated within the outer tubular member while conforming to the bend of the outer tubular member.

8. A flexible inner tubular member as recited in claim 7 wherein said helical cut is disposed around said central longitudinal axis of said inner tube with a right hand turn and said strip of material is wound over said inner tube with a left hand turn.

9. A flexible inner tubular member as recited in claim 8 wherein said strip is made from resilient material.

10. A flexible inner tubular member as recited in claim 9 wherein said strip is made from stainless steel.

11. A flexible inner tubular member as recited in claim 10 wherein said spiral wrap is a first spiral wrap, said strip of material is a first strip of material and further including a second spiral wrap disposed over said first spiral wrap including a second strip of material made from stainless steel wound over said first strip of material and having ends secured to said inner tube, said second strip of material being wound over said first strip of material with a right hand turn.

12. A flexible inner tubular member as recited in claim 7 wherein said cutting member includes a bur tip having an aspiration port communicating with said lumen of said inner tube.

13. A flexible inner tubular member as recited in claim 7 wherein said cutting member includes a cutting window communicating with said lumen of said inner tube and a plurality of cutting teeth extending longitudinally on opposing sides of said cutting window.

14. A flexible inner tubular member for being rotated in a longitudinally bent outer tubular member of a rotary tissue cutting instrument to cut anatomical tissue, said flexible inner tubular member comprising an elongate inner tube of integral one-piece construction having a central longitudinal axis, a rotatably driveable proximal end, a distal end at which a cutting member is disposed to cut anatomical tissue, a cylindrical wall defining a lumen in said inner tube, and a helical cut formed in said inner tube extending along said cylindrical wall in a helical path less than the entire length of said inner tube, said helical cut extending radially through said cylindrical wall to define a plurality of integrally, unitarily connected tube segments angularly movable relative to one another, said helical cut having a pattern defining interlocking tenons and mortises between adjacent ones of said tube segments, said helical cut extending around said central longitudinal axis in a first direction and at a first angle of about 70° with said central longitudinal axis, said helical cut defining a helically cut region in said inner tube having a distal end portion, a proximal end portion and a central portion between said distal and proximal end portions, said helical cut having a uniform first pitch along said central portion and a uniform second pitch, greater than said first pitch, along said distal and proximal end portions;

an inner spiral wrap disposed over said helically cut region and including a flat strip of material wound over said inner tube and having ends secured to said inner tube, said inner spiral wrap being wound around said inner tube in a second direction, opposite said first direction, and at a second angle of about 110° with said central longitudinal axis that is the supplement of said first angle; and an outer second spiral wrap disposed over said inner spiral wrap and including a flat strip of material wound over said inner spiral wrap and having ends secured to said inner tube, said outer spiral wrap being wound over said inner spiral wrap in said first direction and at said first angle with said central longitudinal axis, said helical cut and said outer and inner spiral wraps defining a flexible region in said inner tubular member allowing said inner tubular member to bend while being rotated within the outer tubular member.

15. A rotary tissue cutting instrument comprising an elongate outer tubular member including a proximal portion extending distally from an open proximal end to a bend, and a distal portion extending distally from said bend to an open distal end; and a flexible inner tubular member rotatably disposed in said outer tubular member and including an inner tube of integral one-piece construction having a central longitudinal axis, a rotatably driveable proximal end and a distal end carrying a cutting member exposed from said distal end of said outer tubular member to cut anatomical tissue, said inner tubular member including a flexible region disposed in said bend and being formed by a helical cut formed in said inner tube and a strip of material spirally wrapped over said helical cut and having ends secured to said inner tube, said helical cut extending radially through said inner tube to define a plurality of integrally, unitarily connected tube segments angularly movable relative to one another, said helical cut being formed in a dovetail pattern with adjacent ones of said segments interlocked by at least one tenon in interlocking engagement with at least one mortise, said helical cut being disposed at a first angle of about 70° with said central longitudinal axis and said strip of material being disposed at a second angle of about 110° with said central longitudinal axis that is the supplement of said first angle, said strip of material being wound over said inner tube in a direction opposite said helical cut.

16. A rotary tissue cutting instrument as recited in claim 15 wherein said helical cut is formed by laser cutting said inner tube.

17. A rotary tissue cutting instrument as recited in claim 15 wherein said cutting member includes a bur tip.

18. A rotary tissue cutting instrument as recited in claim 17 wherein said bur tip has an aspiration port communicating with said lumen of said inner tube.

19. A rotary tissue cutting instrument as recited in claim 15 wherein said cutting member includes a cutting port communicating with said lumen of said inner tube and a plurality of cutting teeth extending longitudinally on opposite sides of said culling port.

20. A rotary tissue cutting instrument as recited in claim 15 wherein said strip of material is a first strip of material and said flexible region is further formed by a second strip of material spirally wrapped over said first strip of material and having ends secured to said inner tube, said second strip of material being spirally wrapped around said inner tube in said first direction and being disposed at said first angle with said central longitudinal axis.

21. A rotary tissue cutting instrument comprising elongate outer tubular member means for being introduced at an operative site and including a proximal portion extending distally from an open proximal end to a bend, and a distal portion extending distally from said bend to an open distal end for being positioned adjacent anatomical tissue at the operative site; and flexible inner tubular member means for being rotatably disposed in said outer tubular member means, said inner tubular member means including a rotatably driveable proximal end, a distal end carrying cutting means exposed from said open distal end of said outer tubular member means for cutting the anatomical tissue, integrally and unitarily connected tube segment means juxtaposed with said bend for imparting bending movement to said inner tubular member means, and at least one wrap means wound over said tube segment means for forming, with said tube segment means, a flexible region in said inner tubular member means allowing said inner tubular member means to conform to said bend while being rotated in said outer tubular member means, said tube segment means extending along a segmented region of said inner tubular member means and having a first pitch along a central portion of said segmented region for greater flexibility and having a second pitch, greater than said first pitch, along distal and proximal portions of said segmented region close to said distal and proximal ends, respectively, of said inner tubular member means for greater torsional strength.

* * * * *